US009433377B2

United States Patent
Aoyama et al.

(10) Patent No.: US 9,433,377 B2
(45) Date of Patent: Sep. 6, 2016

(54) SLEEP STATE MANAGEMENT DEVICE, SLEEP STATE MANAGEMENT METHOD, AND SLEEP STATE MANAGEMENT PROGRAM

(71) Applicant: OMRON HEALTHCARE Co., Ltd., Kyoto (JP)

(72) Inventors: Hiroaki Aoyama, Kyoto (JP); Teppei Sumino, Kyoto (JP); Atsushi Sone, Kyoto (JP); Hiroya Nakanishi, Kyoto (JP); Takeshi Kubo, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 0 days.

(21) Appl. No.: 14/388,120

(22) PCT Filed: Nov. 12, 2012

(86) PCT No.: PCT/JP2012/079287
§ 371 (c)(1),
(2) Date: Sep. 25, 2014

(87) PCT Pub. No.: WO2013/145417
PCT Pub. Date: Oct. 3, 2013

(65) Prior Publication Data
US 2015/0029030 A1 Jan. 29, 2015

(30) Foreign Application Priority Data
Mar. 26, 2012 (JP) .................. 2012-069608

(51) Int. Cl.
*A61B 5/11* (2006.01)
*A61B 5/00* (2006.01)
*G01H 1/00* (2006.01)
(Continued)

(52) U.S. Cl.
CPC ............... *A61B 5/4812* (2013.01); *A61B 5/11* (2013.01); *A61B 5/4815* (2013.01); *A61B 5/6892* (2013.01); *A61B 5/7275* (2013.01);
(Continued)

(58) Field of Classification Search
None
See application file for complete search history.

(56) References Cited

U.S. PATENT DOCUMENTS 7,766,841 B2     8/2010   Yamamoto et al.
2004/0034285 A1*   2/2004   Sahashi ..................... 600/300
(Continued)

FOREIGN PATENT DOCUMENTS

CN     101528127 A    9/2009
JP     2006-230789 A    9/2006
(Continued)

OTHER PUBLICATIONS

International Search Report issued in PCT/JP2012/079287 mailed on Dec. 18, 2012 (2 pages).
(Continued)

*Primary Examiner* — Mohamed Barakat
(74) *Attorney, Agent, or Firm* — Osha Liang LLP

(57) ABSTRACT

A sleep state management device includes a sensor that detects movement in bedding where a measurement subject is sleeping, and a control unit that calculates a peak value difference, which is a difference between adjacent peak values in a detection signal outputted from the sensor, determines that a period in which a number of times the peak value difference exceeds a threshold is greater than a predetermined value is a period in which the measurement subject has moved, and manages the sleep state of the measurement based on a result of the determination.

2 Claims, 9 Drawing Sheets

(51) Int. Cl.
  *G01P 15/00* (2006.01)
  *G08B 21/06* (2006.01)

(52) U.S. Cl.
  CPC ............... *G01H 1/00* (2013.01); *G01P 15/00* (2013.01); *G08B 21/06* (2013.01); *A61B 2562/0219* (2013.01)

(56) References Cited

U.S. PATENT DOCUMENTS

| | | | |
|---|---|---|---|
| 2005/0107722 A1* | 5/2005 | Ozaki et al. | 600/587 |
| 2007/0106183 A1* | 5/2007 | Suzuki et al. | 600/595 |
| 2009/0192556 A1* | 7/2009 | Wu et al. | 607/3 |
| 2010/0030118 A1* | 2/2010 | Hiei et al. | 600/595 |
| 2012/0116187 A1* | 5/2012 | Hayes et al. | 600/301 |

FOREIGN PATENT DOCUMENTS

| | | |
|---|---|---|
| JP | 2006-271894 A | 10/2006 |
| JP | 2006-280408 A | 10/2006 |
| JP | 2007-061503 A | 3/2007 |
| JP | 2007-292514 A | 11/2007 |
| JP | 2008-307204 A | 12/2008 |
| WO | 2006/090876 A1 | 8/2006 |
| WO | 2006/123691 A1 | 11/2006 |

OTHER PUBLICATIONS

Written Opinion of the International Searching Authority issued in PCT/JP2012/079287 mailed on Dec. 18, 2012 (6 pages).

Office Action issued in corresponding Chinese Application No. 201280071831.7 dated Aug. 24, 2015, and English translation thereof (17 pages).

* cited by examiner

SLEEP STATE MANAGEMENT DEVICE, SLEEP STATE MANAGEMENT METHOD, AND SLEEP STATE MANAGEMENT PROGRAM

TECHNICAL FIELD

The present invention relates to sleep state management devices, sleep state management methods, and sleep state management programs.

BACKGROUND ART

Ensuring the quality and appropriate state of sleep is essential for maintaining one's health. It is necessary to understand a sleep state, including an amount of sleep time from when a person goes to bed to when the person wakes, the depth of the sleep, and so on, in order to evaluate the sleep state. The devices disclosed in Patent Literature 1-3 have been proposed as devices for understanding such a sleep state.

Patent Literature 1 discloses a device that detects a measurement subject's body movement in a non-contact manner by using an infrared sensor provided in a position distanced from the measurement subject, and determines that a segment, in which a change amount in a signal outputted from the infrared sensor in a short interval of time exceeds a threshold with high frequency, is a segment in which the measurement subject is in a waking state.

Patent Literature 2 discloses a device that detects a measurement subject's body movement using an accelerometer attached to the measurement subject, calculates a fluctuation amount in a detection signal based on a time derivative of the output of the accelerometer, and determines that a segment, in which the fluctuation amount exceeds a threshold with high frequency, is a segment in which the measurement subject is in a waking state.

Patent Literature 3 discloses a device that determines a sleep state of a measurement subject using a vibration sensor that detects vibrations in a location where the measurement subject is sleeping.

CITATION LIST

Patent Literature

Patent Literature 1: JP 2006-280408A
Patent Literature 2: JP 2006-271894A
Patent Literature 3: JP 2007-61503A

SUMMARY OF INVENTION

Technical Problem

When using a sensor to detect vibrations in the location where the measurement subject is sleeping as disclosed in Patent Literature 3, the level of the signal outputted from the sensor is extremely low compared to that from a sensor that directly detects body movement, such as those disclosed in Patent Literature 1 and 2.

Meanwhile, although the methods disclosed in Patent Literature 1 and 2 are suited to configurations having high sensor outputs, such methods have difficulty accurately determining whether or not there is body movement in configurations that detect slight vibrations in the location where a measurement subject is sleeping, as in Patent Literature 3.

Recent years have seen an increase in demand for improving the quality of sleep, and as such there is demand for the development of a device that can accurately determine a sleep state, that can be used with ease in households, and that is not burdensome for measurement subjects.

Having been achieved in light of the aforementioned circumstances, it is an object of the present invention to provide a sleep state management device, a sleep state management method, and a sleep state management program capable of accurately determining whether or not a measurement subject's body is moving.

Solution to Problem

A sleep state management device according to the present invention includes a sensor unit that detects movement in bedding where a measurement subject is sleeping, a peak value difference calculation unit that calculates a peak value difference that is a difference between adjacent peak values in a detection signal outputted from the sensor unit, a first body movement determination unit that determines that a period in which a number of times the peak value difference exceeds a first threshold is greater than a predetermined value is a period in which the measurement subject's body has moved, and a sleep state management unit that manages the measurement subject's sleep state using a result of the determination performed by the first body movement determination unit.

A sleep state management method according to the present invention includes a peak value difference calculation step of calculating a peak value difference that is a difference between adjacent peak values in a detection signal outputted from a sensor unit that detects vibration in bedding in which a measurement subject is sleeping, a body movement determination step of determining that a period in which a number of times the peak value difference exceeds a threshold is greater than a predetermined value is a period in which the measurement subject's body has moved, and a sleep state management step of managing the measurement subject's sleep state using a result of the determination made in the body movement determination step.

A sleep state management program according to the present invention is a program for causing a computer to execute the steps of the aforementioned sleep state management method.

Advantageous Effects of Invention

According to the present invention, a sleep state management device, a sleep state management method, and a sleep state management program capable of accurately determining whether or not a measurement subject's body is moving can be provided.

DESCRIPTION OF EMBODIMENTS

Hereinafter, an embodiment of the present invention will be described with reference to the drawings.

Figure 1:
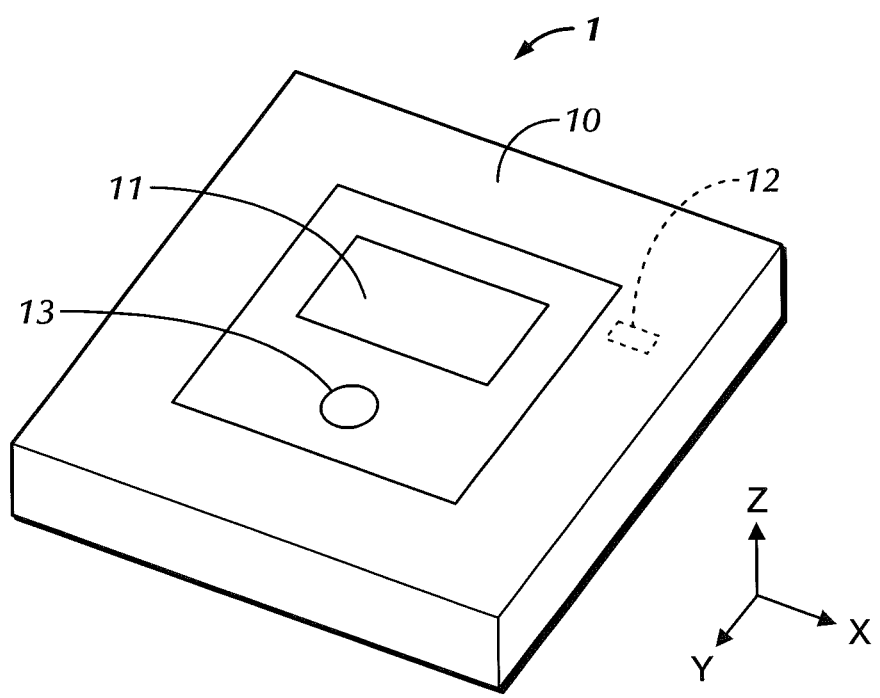
FIG. 1 is an external view illustrating the configuration of a sleep state management device 1 embodying the present invention.

FIG. 1 is an external view illustrating the configuration of a sleep state management device 1 embodying the present invention.

The sleep state management device 1 includes a display unit 11, an operating unit 13, and a sensor 12, which are provided in a box-shaped housing 10.

The display unit 11 and the operating unit 13 are provided in an upper surface (one of two surfaces parallel to an XY plane) of the housing 10. The sensor 12 is provided within the housing 10.

The sleep state management device 1 is used by being placed on a measurement subject's bedding, such as a bed or a futon, with a base surface (the other of the two surfaces parallel to the XY plane) of the housing 10 making contact with the bedding.

The display unit 11 displays various types of menus and the like of the sleep state management device 1, and is configured of a liquid-crystal display device, for example.

The operating unit 13 is an interface for powering the sleep state management device 1 on, making various types of operations, and so on, and is configured of a button or the like, for example.

The sensor 12 is a three-axis accelerometer, and detects an acceleration in an X-axis direction, an acceleration in a Y-axis direction, and an acceleration in a Z-axis direction.

A detection signal resulting from detection performed by the sensor 12 when the sleep state management device 1 is placed on the bedding corresponds to movement (vibration) in the bedding. In other words, the sensor 12 functions as a vibration detection sensor that detects movement in the bedding that the measurement subject is sleeping on.

In this manner, the sensor 12 detects movement in the bedding produced when the measurement subject moves. Movement in the bedding produced when the measurement subject's body moves is slighter than the measurement subject's body movement itself. Accordingly, the level of the detection signal resulting from detection performed by the sensor 12 is extremely low.

Figure 2:
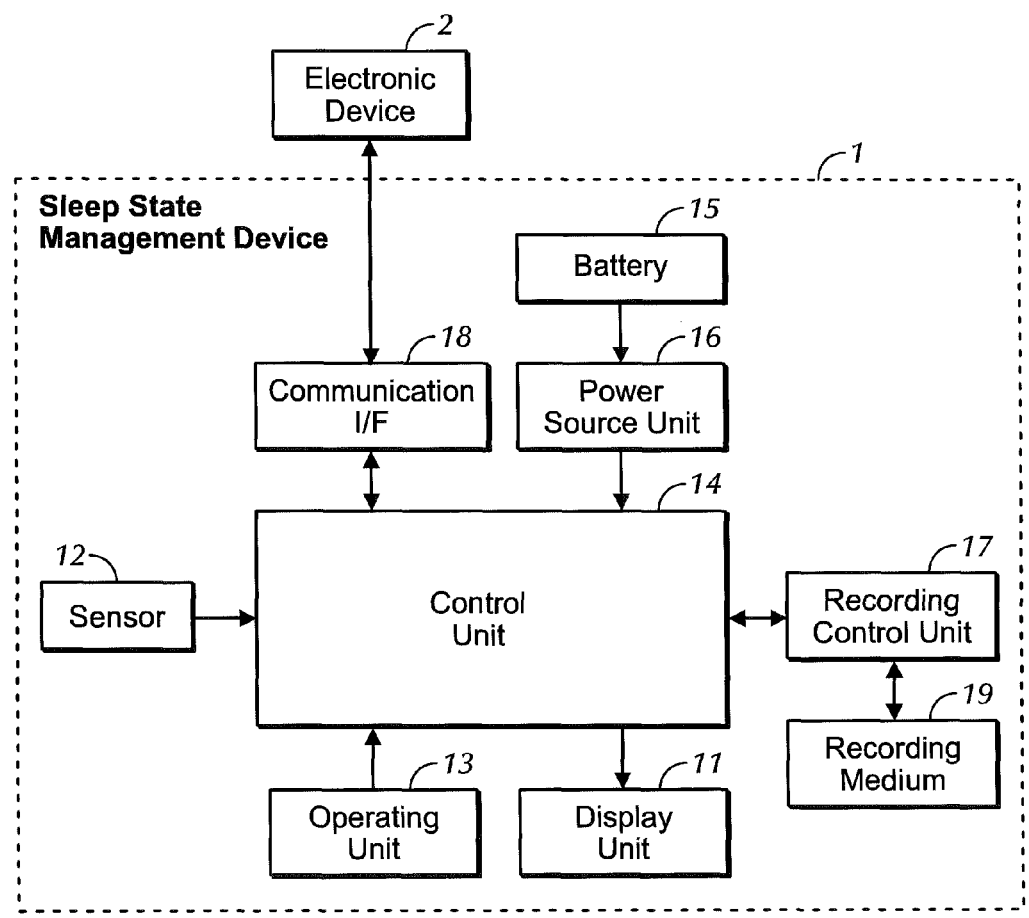
FIG. 2 is a block diagram illustrating the internal configuration of the sleep state management device 1 shown in FIG. 1.

FIG. 2 is a block diagram illustrating the internal configuration of the sleep state management device 1 shown in FIG. 1.

In addition to the display unit 11, the sensor 12, and the operating unit 13 shown in FIG. 1, the sleep state management device 1 includes a battery 15, a power source unit 16, a recording control unit 17, a communication interface (I/F) 18, a recording medium 19, and a control unit 14 that performs various types of computational processes and controls the sleep state management device 1 as a whole.

The battery 15 is a button battery, for example. The power source unit 16 supplies power from the battery 15 to the various units in the sleep state management device 1 via the control unit 14.

The recording medium 19 records data generated by the control unit 14, and is configured of a flash memory or the like, for example.

The recording control unit 17 is a driver for the recording medium 19, and writes data into the recording medium 19 and reads data out from the recording medium 19 in response to instructions from the control unit 14.

The communication I/F 18 is an interface for the sleep state management device 1 to communicate, wirelessly or over wires, with an external electronic device 2 (a personal computer, a mobile phone such as a smartphone, or the like).

The detection signal from the sensor 12 is converted into a digital signal and inputted into the control unit 14. The control unit 14 is configured primarily of a CPU (a central processing unit), carries out various types of computational processes based on the inputted detection signal, and records data based on the results of the computational processes into the recording medium 19.

The operating unit 13 is connected to the control unit 14; a signal resulting from the operating unit 13 being operated is inputted into the control unit 14, and the control unit 14 carries out control based on that signal. The control unit 14 also includes a ROM that stores programs executed by the CPU, a RAM serving as a work memory, and so on.

Operations of the sleep state management device 1 will be described next.

Figure 3:
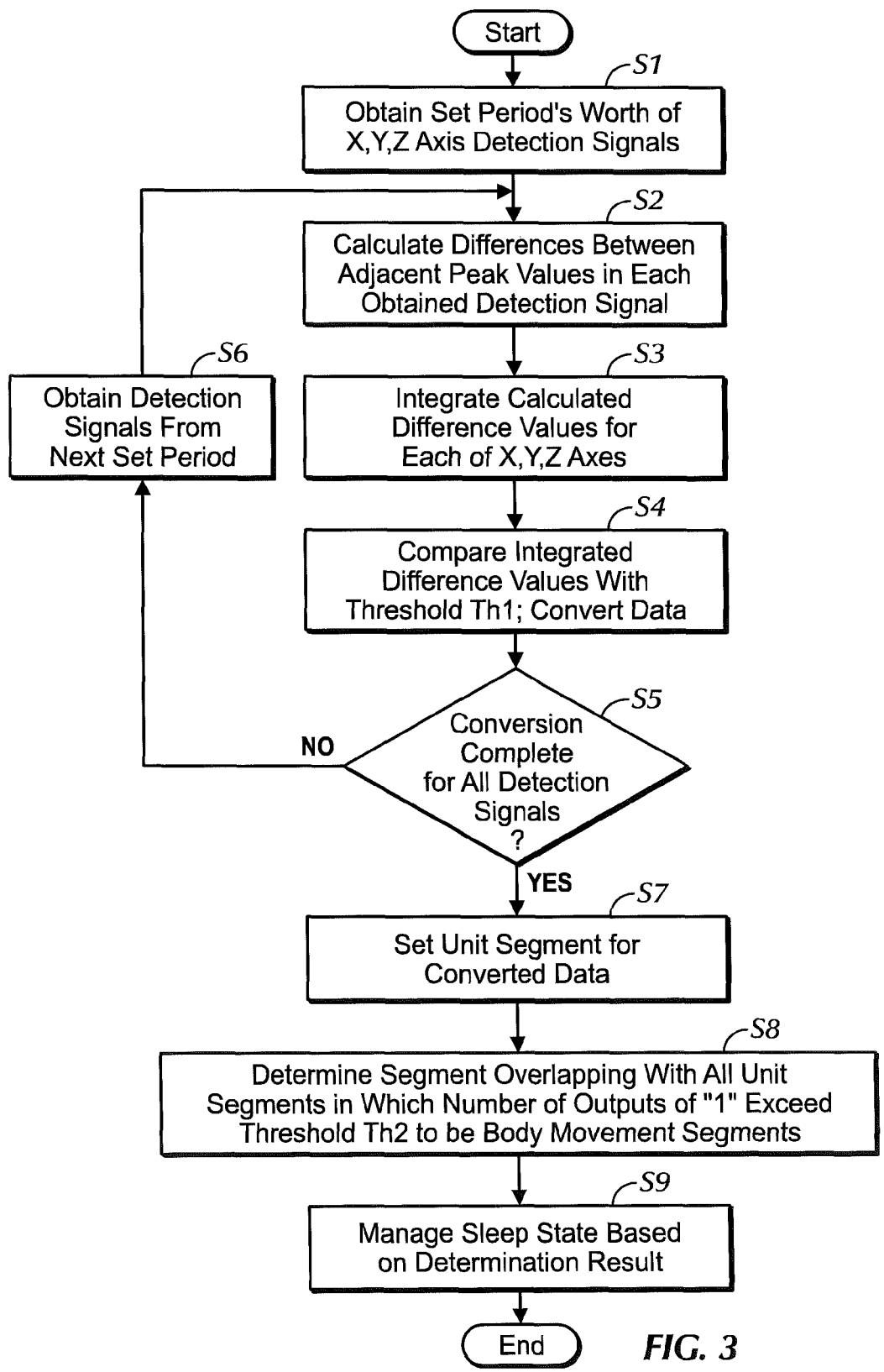
FIG. 3 is a flowchart illustrating operations performed by the sleep state management device 1 shown in FIG. 1.

FIG. 3 is a flowchart illustrating operations performed by the sleep state management device 1 shown in FIG. 1. The respective steps shown in FIG. 3 are carried out by the CPU in the control unit 14 based on programs stored in the ROM.

The measurement subject places the sleep state management device 1 on the bedding and makes an instruction to start recording the sleep state by operating the operating unit 13. When the instruction to start recording has been made, the detection signal resulting from detection performed by the sensor 12 (a digital value) is stored in the RAM of the control unit 14. Note that in the case where an instruction to stop recording the sleep state has been made by the operating unit 13 being operated, the storage of the detection signal in the RAM is stopped.

When a certain amount of the detection signal has been accumulated in the RAM, the control unit 14 obtains, from the detection signal stored in the RAM, a set period's worth (here, 14 seconds, for example) of the detection signal (an X-axis detection signal, a Y-axis detection signal, and a Z-axis detection signal) (step S1).

Next, the control unit 14 calculates, from the obtained detection signals in the respective axes, differences between adjacent peak values (absolute values that disregard the positive/negative sign) (step S2).

Figure 4:
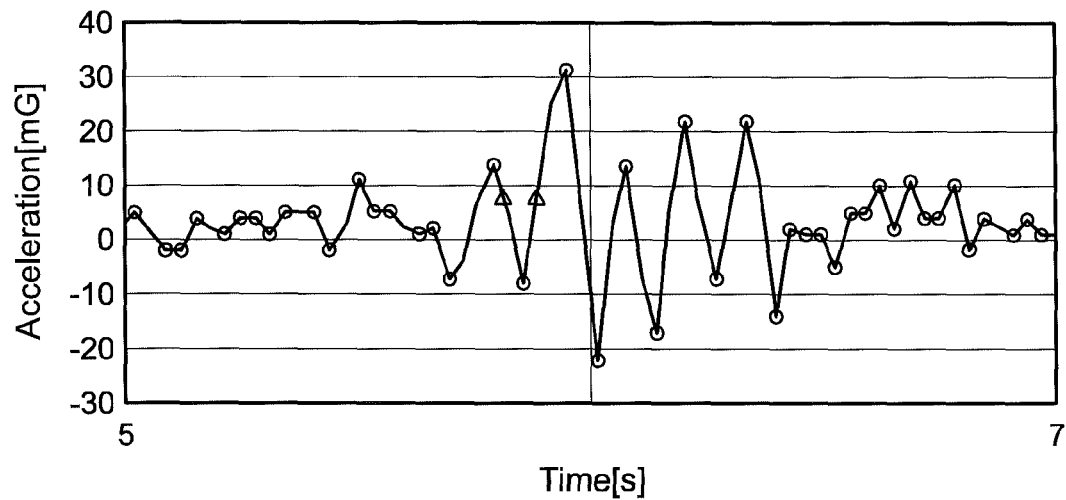
FIG. 4 is a diagram illustrating details of the process performed in step S2 of the flowchart shown in FIG. 3.

FIG. 4 is a diagram illustrating details of the process performed in step S2 of the flowchart shown in FIG. 3. FIG. 4 illustrates a waveform of the obtained (X-axis) detection signal, from seconds number 5 to 7 in the aforementioned set period (of 14 seconds).

In the aforementioned step S2, the control unit 14 first extracts the peak values from the detection signal shown in FIG. 4.

The "peak values" are the values at points where the detected acceleration value switches from a high value to a lower value, levels out from a high value, switches from a low value to a higher value, and levels out from a low value (the points encircled by dotted lines in FIG. 4).

After extracting the peak values, the control unit 14 calculates a difference between each peak value and the peak values adjacent to that peak value (the adjacent peak values obtained before and after the stated peak value when taken in time series).

The control unit 14 then stores the calculated difference values in association with a time represented by a predetermined small segment (a segment approximately equal to an estimated amount of time between peak values) that contains the time at which the peak value was obtained (the stated time being one of a start time, an end time, a midpoint time of the small segment, or the like).

The control unit 14 then integrates difference values in the X-axis detection signal, difference values in the Y-axis detection signal, and difference values in the Z-axis detection signal found in step S2 that correspond to the same time, and finds integrated values of the X-axis, Y-axis, and Z-axis difference values at each time (step S3).

Figure 5:
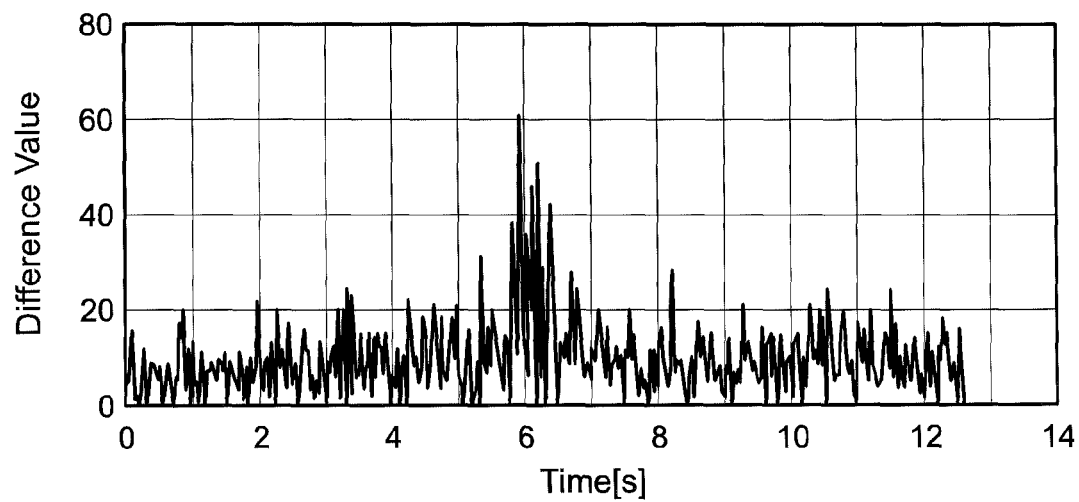
FIG. 5 is a diagram illustrating an example of integrated difference values obtained in step S3 of the flowchart shown in FIG. 3.

FIG. 5 is a diagram illustrating an example of integrated difference values obtained in step S3 of the flowchart shown in FIG. 3. FIG. 5 is a graph in which the integrated values of the difference values throughout the stated set period (14 seconds) have been plotted.

Figure 6:
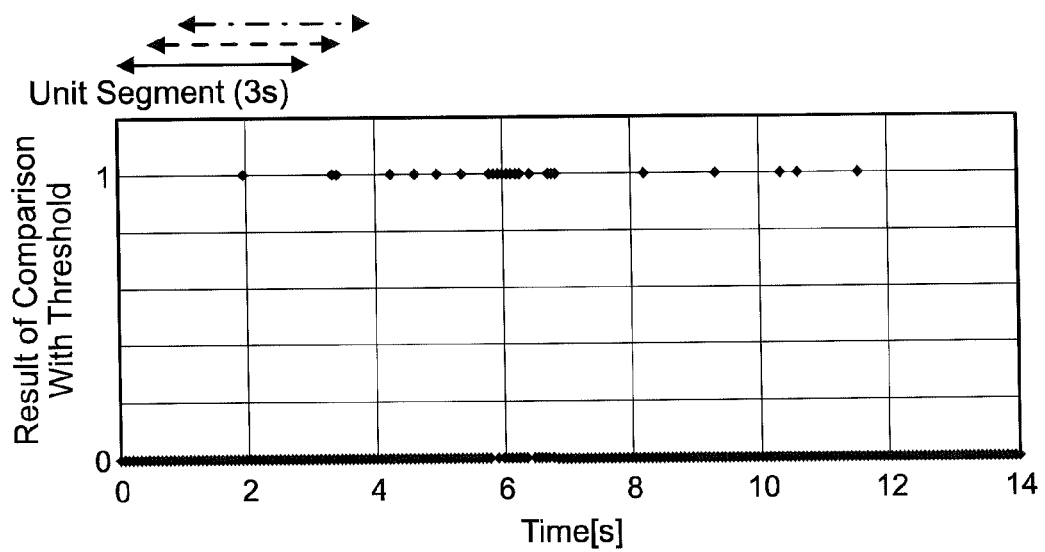
FIG. 6 is a diagram illustrating an example of data obtained in step S4 of the flowchart shown in FIG. 3.

Next, the control unit 14 compares the difference values found in step S3 with a threshold Th1, creates data, shown in FIG. 6, by converting data at times where the difference value exceeds the threshold to "1" and converting data at times where the difference value is less than or equal to the threshold to "0" (step S4), and stores the created data in the RAM. FIG. 6 illustrates data obtained when the threshold Th1 is set to 20 for the data shown in FIG. 5.

For the difference values found in step S3, a greater value indicates a greater change in movement in the bedding where the measurement subject is sleeping.

The bedding moves not only due to the measurement subject moving, but also due to vibrations in the location where the bedding is placed. The sleep state management device 1 uses the sensor 12 to detect slight movements in the bedding.

As such, the detection signals from the sensor 12 also include signals resulting from vibrations in the location where the bedding is placed. The detection signals from the sensor 12 also contain noise unique to the sensor.

Such variations in the detection signal caused by vibrations in the location where the bedding is placed, noise unique to the sensor, and so on are extremely small compared to fluctuations in the detection signal caused by the measurement subject moving.

However, according to the sleep state management device 1, the influence of vibrations in the location where the bedding is placed, noise unique to the sensor, and so on is eliminated by comparing the difference values to the threshold Th1.

In other words, the sleep state management device 1 determines that the bedding is moving due to vibrations in the location where the bedding is placed, noise unique to the sensor, and so on at times when the data is less than or equal to the threshold Th1 of 20 in FIG. 5, and determines that it is likely that the bedding is moving due to the measurement subject moving at times where the data is greater than the threshold Th1 of 20 in FIG. 5.

As shown in FIG. 5, the stated difference values sometimes increase sporadically, and sometimes increase for a sustained period. It is known that a measurement subject's body movements occur for sustained periods, and thus sporadic increases in the difference values can be determined to be caused by factors aside from such body movements.

Accordingly, the control unit 14 determines whether or not the measurement subject is moving through step S8, which will be described later.

After step S4, the control unit 14 carries out the process of step S7 in the case where all of the detection signals stored in the RAM have undergone the processing of step S2 to step S4 (step S5: YES).

On the other hand, in the case where all of the detection signals stored in the RAM have not undergone the processing of step S2 to step S4 (step S5: NO), in step S6, the control unit 14 obtains the detection signals of the next set period (a period from seconds 14 to 28, for example) from the RAM and carries out the processing from step S2 on.

In step S7, the control unit 14 sets a unit segment (for example, a three-second segment) for the converted data generated in step S4 every 0.5 seconds, for example.

That is, the control unit 14 sets the unit segments so as to be staggered by 0.5 seconds, resulting in a segment indicated by a solid line arrow in FIG. 6 (a segment from seconds 0 to 3), a segment indicated by a broken line arrow in FIG. 6 (a segment from seconds 0.5 to 3.5), a segment indicated by a dot-dash line arrow in FIG. 6 (a segment from seconds 1 to 4), and so on.

After step S7, the control unit 14 counts the number of pieces of data that are "1" in each unit segment that has been set, and determines that segments in which the number of pieces of data that are "1" is greater than a threshold Th2 are segments in which the measurement subject has moved, and that segments in which the number of pieces of data that are "1" is less than or equal to the threshold Th2 are segments in which the measurement subject has not moved.

Then, the control unit 14 determines that periods overlapping with all of the unit segments determined to contain body movement are periods of body movement, and that other periods are periods without body movement (step S8).

Next, the control unit 14 manages the measurement subject's sleep state based on the result of the determination made in step S8 (step S9).

Specifically, the control unit 14 manages the measurement subject's sleep state by recording, into the recording medium 19, data indicating a period in which the frequency at which body movement occurs is greater than or equal to a predetermined threshold as a waking state period and a period in which the frequency at which body movement occurs is less than the predetermined threshold as a sleep state period.

The data indicating the measurement subject's sleep state can be recorded into the recording medium 19 and the measurement subject's sleep state can be managed through the operations described thus far.

In this manner, the sleep state management device 1 calculates differences between adjacent peak values in the detection signal from the sensor 12 and determines whether or not there is body movement based on the difference values.

The devices disclosed in Patent Literature 1 and 2 determine whether or not there is body movement based on differences between the values of signals sequentially outputted from a sensor and the values of the signals outputted immediately before the stated signals. In other words, these differences may be differences between values aside from the peak values in the detection signal from the sensor.

To use the example of FIG. 4, in the case where differences are found between the values indicated by the triangles, it will be erroneously determined that there are no variations in the detection signal.

Such erroneous determinations do not occur easily when the cycle of the detection signal from the sensor is long; however, the cycle of the detection signal is extremely short in the case where a sensor that detects vibrations in the bedding is used, as with the sleep state management device 1, making it difficult to reduce such erroneous determinations.

Accordingly, by calculating differences between adjacent peak values in the detection signal from the sensor 12 as described above, even slight movement in the bedding can be detected and missing such movement can be avoided, which improves the accuracy at which whether or not there is body movement is determined.

Furthermore, according to the sleep state management device 1, a three-axis accelerometer is used as the sensor 12, and after the difference values found for the three axes are integrated in step S4 of FIG. 3, whether or not there is body movement is determined based on the integrated difference values; therefore, the determination as to whether or not there is body movement can be carried out having emphasized the difference values, which makes it possible to improve the accuracy of the determination.

Note that any sensor capable of detecting movement in the bedding can be used as the sensor 12 provided in the sleep state management device 1; the sensor is thus not limited to an accelerometer, and the sensors described in Patent Literature 3 may be used as well.

However, using an accelerometer makes it possible to detect movement in the bedding by carrying out the simple task of placing the sleep state management device 1 on the bedding, which makes it possible to reduce the burden placed on the measurement subject.

In the case where sensor that outputs only a single type of detection signal, such as a single-axis accelerometer, is used as the sensor 12, the process of step S3 in FIG. 3 can be omitted, and in step S4, the data conversion may be carried out by comparing the difference values calculated in step S2 with the threshold Th1.

Although the foregoing describes determining whether or not there is body movement after carrying out the processes of step S2 to step S4 on all of the detection signals, the processes of steps S7 to 9 may be carried out in parallel with the processes of step S2 to step S4.

By doing so, the control unit 14 can distinguish between the waking state and the sleep state while obtaining the detection signal, and thus in the case where, for example, the stated waking state period has been determined near a pre-set time, an alarm can be activated and the measurement subject can be prompted to wake in a favorable manner.

In this manner, the sleep state management carried out by the control unit 14 is not limited to recording data expressing the sleep state, and also includes applying some sort of stimulus to the measurement subject in accordance with the sleep state.

A variation on the sleep state management device 1 will be described next.

Figure 7:
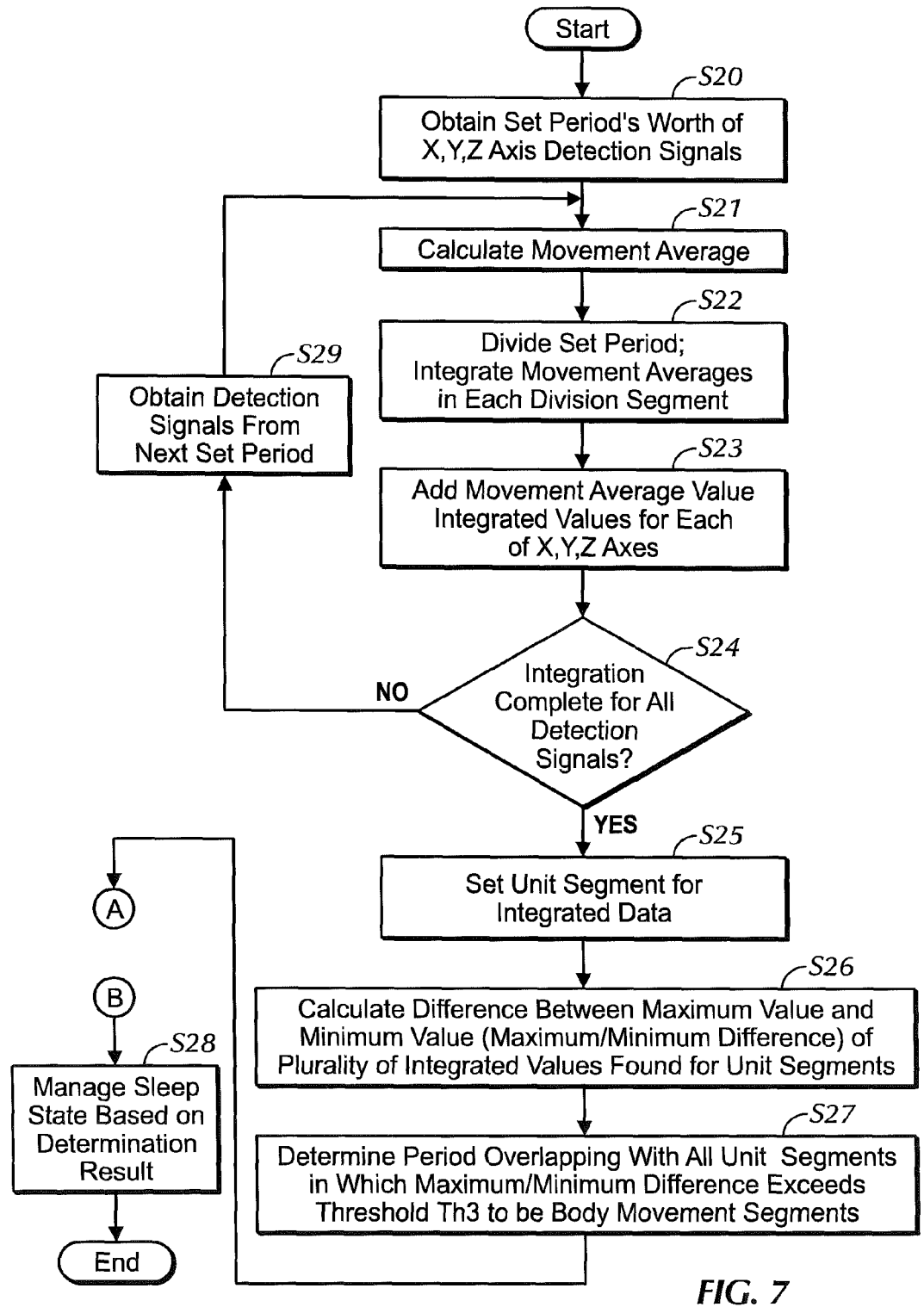
FIG. 7 is a flowchart illustrating a variation on operations performed by the sleep state management device 1 shown in FIG. 1.
Figure 8:
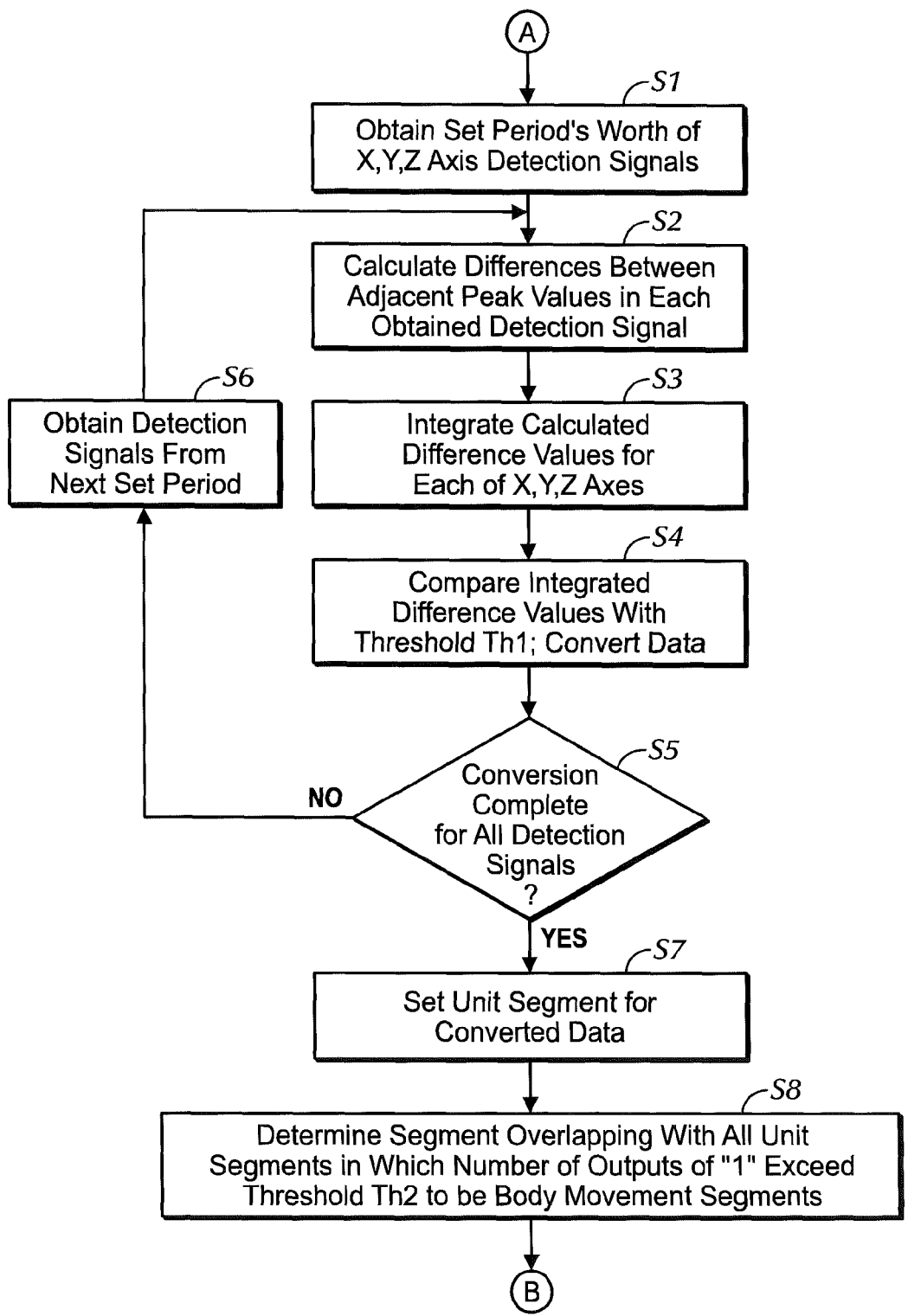
FIG. 8 is a flowchart illustrating a variation on operations performed by the sleep state management device 1 shown in FIG. 1.

FIGS. 7 and 8 are flowcharts illustrating a variation on operations performed by the sleep state management device 1 shown in FIG. 1.

When an instruction to start recording the sleep state has been made, the detection signal resulting from detection performed by the sensor 12 (a digital value) is stored in the RAM of the control unit 14.

When a certain amount of the detection signal has been accumulated in the RAM, the control unit 14 obtains, from the detection signal stored in the RAM, a set period's worth (here, 14 seconds, for example) of the detection signal (an X-axis detection signal, a Y-axis detection signal, and a Z-axis detection signal) (step S20).

After obtaining the set period's worth of the detection signal in step S20, the control unit 14 calculates a movement average for the obtained detection signal in each axis (step S21).

Figure 9:
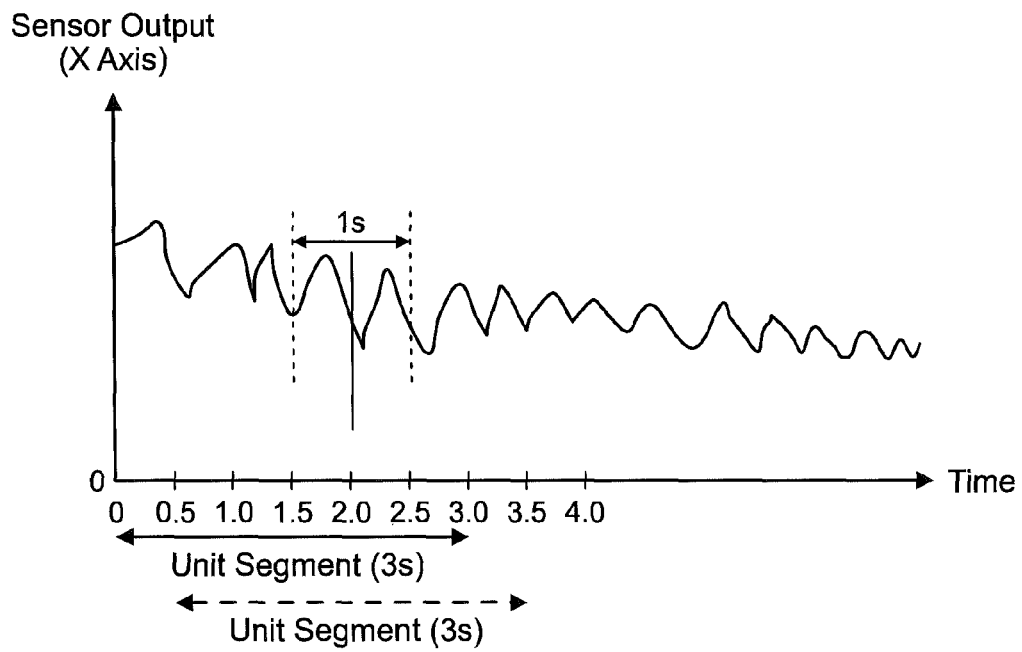
FIG. 9 is a diagram illustrating details of the process performed in step S21 of the flowchart shown in FIG. 7.

FIG. 9 is a diagram illustrating details of the process performed in step S21 of the flowchart shown in FIG. 7. FIG. 9 illustrates a waveform of the detection signal (for the X axis) obtained in step S20.

For example, the control unit 14 calculates, for a time that is a multiple of 0.1 seconds, an average value of the detection signal in a range of 0.5 seconds before and after that time (the range between the two dotted lines shown in FIG. 9, for example) as the movement average value at that time.

Noise (a high-frequency component) that is unrelated to the measurement subject's body movement can be removed through the processing of step S21.

Next, the control unit 14 divides the stated set period in segments of, for example, 0.5 seconds, and carries out a process that integrates the five movement average values corresponding to each of the division segments, on the detection signal from each axis (step S22).

Figure 10:
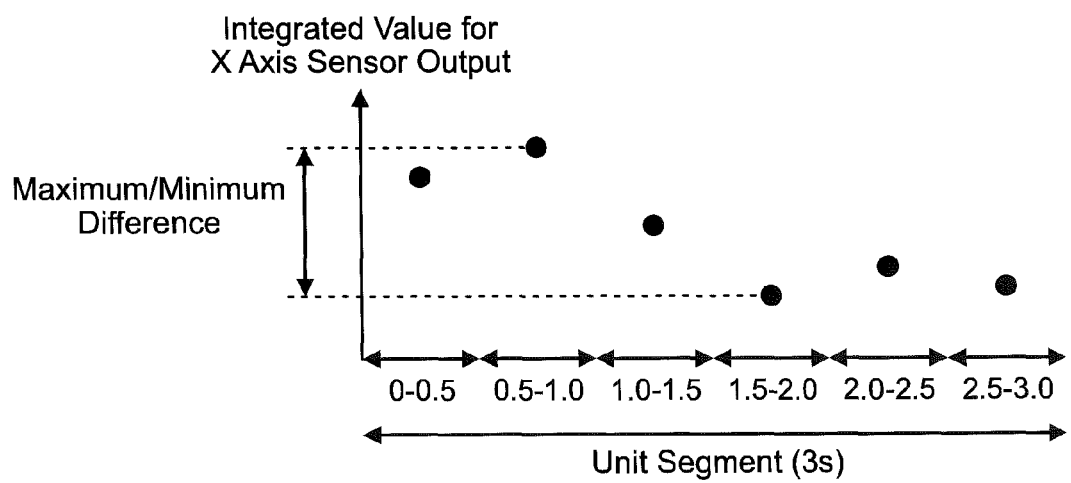
FIG. 10 is a diagram illustrating details of the process performed in step S22 of the flowchart shown in FIG. 7.

A single integrated value is found for each of the division segments as a result of this process, as indicated in FIG. 10, for example. Carrying out the process of step S22 makes it possible to reduce the degree of influence of noise that could not be removed through the process of step S21.

Next, the control unit 14 adds the integrated value for the X axis detection signal, the integrated value for the Y axis detection signal, and the integrated value for the Z axis detection signal, that have been found for each of the division segments (step S23).

After step S23, the control unit 14 carries out the processing from step S25 on in the case where all of the detection signals stored in the RAM have undergone the processing of step S21 to step S23 (step S24: YES).

On the other hand, in the case where all of the detection signals stored in the RAM have not undergone the processing of step S21 to step S23 (step S24: NO), in step S29, the control unit 14 obtains the detection signals of the next set period (a period from seconds 14 to 28, for example) from the RAM and carries out the processing from step S21 on.

In step S25, the control unit 14 sets a plurality of unit segments (three-second segments, for example), whose start times are shifted from each other by 0.5 seconds, in the data generated in step S23.

For example, as shown in FIG. 9, the unit segments are set so as to produce a segment from seconds 0 to 3, as indicated by a solid line arrow, a segment from seconds 0.5 to 3.5, as indicated by a broken line arrow, and so on.

Next, the control unit 14 calculates a maximum/minimum difference, which is a difference between a maximum value and a minimum value (absolute values that disregard the positive/negative sign) among the six integrated values (sum values for the X, Y, and Z axes) corresponding to the six division segments contained in each of the set unit segments, as shown in FIG. 10 (step S26).

Figure 11:
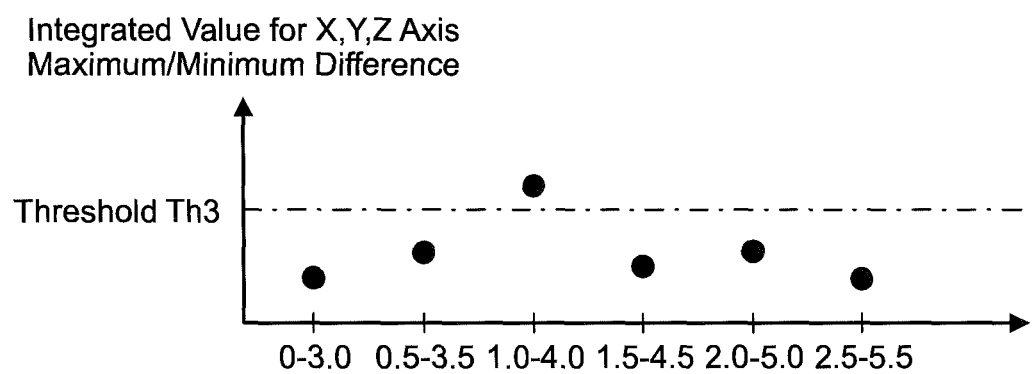
FIG. 11 is a diagram illustrating details of the process performed in step S27 of the flowchart shown in FIG. 7.

Through the process of step S26, the maximum/minimum difference is found for each of the unit segments, as shown in FIG. 11.

After step S26, the control unit 14 determines that a unit segment in which the maximum/minimum difference exceeds a threshold Th3 (the segment from seconds 1 to 4 in the example shown in FIG. 11) is a segment of body movement, and determines that a unit segment in which the maximum/minimum difference is less than or equal to the threshold Th3 is a segment without body movement.

Then, the control unit 14 determines that periods overlapping with all of the unit segments determined to contain body movement are periods of body movement, and that other periods are periods without body movement (step S27).

After step S27, the control unit 14 carries out the processes of step S1 to step S8 in FIG. 3, and then carries out the process of step S28.

In step S28, the control unit 14 manages the measurement subject's sleep state using the determination result from step S27 and the determination result from step S8.

For example, the control unit 14 sets a period combining the period determined to have body movement in step S27 and the period determined to have body movement in step S8 as a period of body movement, and sets other periods as periods without body movement.

Then, the control unit 14 manages the measurement subject's sleep state by recording, into the recording medium 19, data indicating a period in which the frequency at which body movement occurs is greater than or equal to a predetermined threshold as a waking state period and a period in which the frequency at which body movement occurs is less than the predetermined threshold as a sleep state period.

As described thus far, according to this variation, body movement in the measurement subject can be determined with a high level of accuracy through the processing of step S20 to step S27 in FIG. 7, even if the detection signal has an extremely low level.

Furthermore, because the presence/absence of body movement is ultimately determined using the determination result from step S27 in FIG. 7 and the determination result from step S8 in FIG. 8, the accuracy with which the presence/absence of body movement is determined can be increased by combining the two techniques.

According to the processes of step S1 to step S8 in FIG. 8, the presence/absence of body movement is determined based on the difference between adjacent peak values in the detection signal from the sensor 12, and thus body movement can be detected with a high degree of accuracy even in cases where a measurement subject having a low body weight is sleeping on bedding that does not easily vibrate.

Although the processes of step S20 to step S27 in FIG. 7 and the processes of step S1 to step S8 in FIG. 8 are carried out separately here, it should be noted that these processes may be carried out in parallel. The order of these processes may be reversed as well.

Furthermore, a user of the sleep state management device 1 may be made able to select which of the processes to carry out.

For example, the amount of computations can be reduced through the processes of step S20 to step S27 in FIG. 7 as compared to the processes of step S1 to step S8 in FIG. 8, and thus the lifespan of the battery in the sleep state management device 1 can be extended by using the flow that moves to step S28 after step S27 in FIG. 7 when a power-saving mode has been enabled.

Furthermore, the remaining battery power of the sleep state management device 1 may be monitored, and either the processes of step S20 to step S27 in FIG. 7 or the processes of step S1 to step S8 in FIG. 8 may be carried out in the case where little battery power remains; data based on the determination result from the processes that have been carried out may then be recorded into the recording medium 19.

The process of step S22 in FIG. 7 may be omitted. In this case, the difference between the maximum value and the minimum value of movement average values calculated for the unit segments may be calculated in step S26.

In addition, in the case where, for example, a single-axis accelerometer is used as the sensor 12, the process of step S23 in FIG. 7 may be omitted.

The respective steps illustrated in FIGS. 3, 7, and 8 and executed by the control unit 14 of the sleep state management device 1 can also be executed by the electronic device 2 connected to the sleep state management device 1.

In this case, a program for causing a computer to execute the respective steps shown in FIGS. 3, 7, and 8 and carried out by the control unit 14 of the sleep state management device 1 may be installed in the electronic device 2. Such a program is then recorded in a non-transitory recording medium from which the computer can read the program.

This computer-readable recording medium includes optical media such as a Compact Disc-ROM (CD-ROM), magnetic recording media such as memory cards, and so on. Further still, the program can be downloaded via a network and provided in such form.

Note that the embodiment disclosed above is to be understood as being in all ways exemplary and in no way limiting. The scope of the present invention is defined not by the aforementioned descriptions but by the scope of the appended claims, and all changes that fall within the same essential spirit as the scope of the claims are intended to be included therein as well.

As described thus far, the following items are disclosed in the present specification.

A sleep state management device disclosed here includes a sensor unit that detects movement in bedding where a measurement subject is sleeping, a peak value difference calculation unit that calculates a peak value difference that is a difference between adjacent peak values in a detection signal outputted from the sensor unit, a first body movement determination unit that determines that a period in which a number of times the peak value difference exceeds a first threshold is greater than a predetermined value is a period in which the measurement subject's body has moved, and a sleep state management unit that manages the measurement subject's sleep state using a result of the determination performed by the first body movement determination unit.

The sleep state management device disclosed here includes a configuration in which the sensor unit is a two- or three-axis accelerometer.

The sleep state management device disclosed here includes a configuration in which the peak value difference is an integrated value of the differences calculated for detection signals from each axis outputted from the sensor unit.

The sleep state management device disclosed here further includes a maximum/minimum difference calculation unit that finds, for each of unit segments in a period in which the detection signal is outputted from the sensor unit, a maximum/minimum difference that is a difference between a maximum value and a minimum value in the detection signal in the unit segment, and a second body movement determination unit that determines that the unit segment in which the maximum/minimum difference exceeds a second threshold is a segment in which the measurement subject's body has moved; here, the sleep state management unit manages the measurement subject's sleep state using a result of the determination performed by the first body movement determination unit and a result of the determination performed by the second body movement determination unit.

The sleep state management device disclosed here further includes an integrated value calculation unit that calculates, for each of divided segments obtained by dividing the unit segment, an integrated value of the detection signal obtained every set amount of time; here, the maximum/minimum difference calculation unit calculates a difference between the maximum value and the minimum value of a plurality of integrated values calculated for each of the unit segments as the maximum/minimum difference.

A sleep state management method disclosed here includes a peak value difference calculation step of calculating a peak value difference that is a difference between adjacent peak values in a detection signal outputted from a sensor unit that detects vibration in bedding in which a measurement subject is sleeping, a body movement determination step of determining that a period in which a number of times the peak value difference exceeds a threshold is greater than a predetermined value is a period in which the measurement subject's body has moved, and a sleep state management step of managing the measurement subject's sleep state using a result of the determination made in the body movement determination step.

A sleep state management program disclosed here is a program for causing a computer to execute the steps of the aforementioned sleep state management method.

INDUSTRIAL APPLICABILITY

The present invention can be applied in household sleep management devices, for example, and is useful in managing a user's health.

While the present invention has been described in detail with reference to a specific embodiment, it will be clear to one of ordinary skill in the art that many variations and modifications can be made without departing from the essential spirit and scope of the present invention. This application claims the benefit of Japanese Patent Application No. 2012-69608, filed Mar. 26, 2012, which is hereby incorporated by reference herein in its entirety.

REFERENCE SIGNS LIST 1 sleep state management device
11 display unit
12 sensor
13 operating unit
14 control unit

The invention claimed is:

1. A sleep state management method comprising:
a peak value difference calculation step of calculating a peak value difference that is a difference between adjacent peak values in a detection signal outputted from a sensor unit that detects vibration of a bed in which a measurement subject is sleeping;
a first body movement determination step of determining that a period in which a number of times the peak value difference exceeds a threshold is greater than a predetermined value is a period in which the sensor unit has detected vibration, said period including a plurality of unit segment periods;
a sleep state recording step of recording the sleep state of the measurement subject using a result of the determination made in the first body movement determination step;
a maximum/minimum difference calculation step of finding a maximum/minimum difference that is a difference between a maximum value and a minimum value in the detection signal in each unit segment period; and
a second body movement determination step of determining that the unit segment period in which the maximum/minimum difference exceeds a second threshold is a segment period in which the measurement subject's body has moved,
wherein the sleep state recording step further comprises recording the sleep state of the measurement subject using a result of the second body movement determination step.

2. A sleep state management program stored on a non-transitory computer-readable medium for causing a computer to execute the steps of the sleep state management method according to claim 1.

* * * * *